(12) United States Patent
Gombert et al.

(10) Patent No.: US 9,681,921 B2
(45) Date of Patent: Jun. 20, 2017

(54) ROBOT SYSTEM AND METHOD FOR CONTROLLING A ROBOT SYSTEM FOR MINIMALLY INVASIVE SURGERY

(71) Applicant: GOMTEC GmbH, Seefeld (DE)

(72) Inventors: Bernd Gombert, Worthsee (DE); Patrick Rothfuβ, Halbergmoos (DE); Leopold Krausen, Munich (DE)

(73) Assignee: ABB gomtec GmbH, Seefeld (DE)

( * ) Notice: Subject to any disclaimer, the term of this patent is extended or adjusted under 35 U.S.C. 154(b) by 79 days.

(21) Appl. No.: 14/762,208

(22) PCT Filed: Jan. 16, 2014

(86) PCT No.: PCT/EP2014/050779
§ 371 (c)(1),
(2) Date: Jul. 21, 2015

(87) PCT Pub. No.: WO2014/114551
PCT Pub. Date: Jul. 31, 2014

(65) Prior Publication Data
US 2015/0359597 A1    Dec. 17, 2015

(30) Foreign Application Priority Data
Jan. 22, 2013  (DE) .................. 10 2013 100 605

(51) Int. Cl.
*A61B 1/04* (2006.01)
*A61B 19/00* (2006.01)
(Continued)

(52) U.S. Cl.
CPC .......... *A61B 19/2203* (2013.01); *A61B 34/30* (2016.02); *A61B 34/32* (2016.02);
(Continued)

(58) Field of Classification Search
CPC .......... B25J 9/1676; B25J 9/1682; B25J 9/16; Y10S 901/08; A61B 34/00; A61B 34/30
See application file for complete search history.

(56) References Cited

U.S. PATENT DOCUMENTS

| 2002/0082612 | A1* | 6/2002 | Moll ................. A61B 19/2203 606/130 |
| 2007/0173975 | A1 | 7/2007 | Schena |

(Continued)

FOREIGN PATENT DOCUMENTS

| DE | 602004004995 T2 | 11/2007 |
| JP | 2010099403 | 5/2010 |

OTHER PUBLICATIONS

Office Action in corresponding DE Application No. 10 2013 100 605.1 dated Sep. 23, 2013.
(Continued)

*Primary Examiner* — Robert N Wieland
(74) *Attorney, Agent, or Firm* — Manelli Selter PLLC; Edward J. Stemberger (57) ABSTRACT

The invention relates to a method for controlling a robot system (1) for minimally invasive surgery, which comprises at least two robots (2, 3). According to the invention a port (7), which serves to provide access into the body of a patient (5), is operated by means of a first robot (2), and a surgical instrument (10), which is designed to be introduced into the body of the patient (5) through the port (7), is operated by means of a second robot (3). The separate operation of the port (7) and the surgical instrument (10) makes it possible to guide the port (7) synchronously to a movement of the surgical instrument (10), to damp the movement of the surgical instrument (10) or to block the movement by fixing the port (7).

17 Claims, 6 Drawing Sheets

(51) Int. Cl.
- *B25J 9/00*      (2006.01)
- *B25J 9/16*      (2006.01)
- *A61B 34/32*     (2016.01)
- *A61B 34/35*     (2016.01)
- *A61B 17/00*     (2006.01)
- *A61B 34/30*     (2016.01)

(52) U.S. Cl.
CPC ............. *A61B 34/35* (2016.02); *B25J 9/0084* (2013.01); *B25J 9/0087* (2013.01); *B25J 9/1676* (2013.01); *B25J 9/1682* (2013.01); *A61B 2017/00477* (2013.01); *A61B 2034/301* (2016.02); *G05B 2219/39109* (2013.01); *G05B 2219/45117* (2013.01); *Y10S 901/08* (2013.01)

(56) References Cited

U.S. PATENT DOCUMENTS

| | | |
|---|---|---|
| 2010/0234856 A1 | 9/2010 | Stoianovici |
| 2011/0178477 A1 | 7/2011 | Morel et al. |

OTHER PUBLICATIONS

International Search Report in PCT/EP2014/050779 dated Apr. 10, 2014.

\* cited by examiner

ROBOT SYSTEM AND METHOD FOR CONTROLLING A ROBOT SYSTEM FOR MINIMALLY INVASIVE SURGERY

The invention relates to a method for controlling a robot system for minimally invasive surgery, with at least two robots according to the preamble of claim 1, a control device for controlling at least two robots of a robot system according to the preamble of claim 15, and a robot system with such a control device according to the preamble of claim 16.

Surgical interventions on the human body are performed to an increasing extent nowadays using surgical robot-supported minimally invasive techniques. Depending upon the nature of the intervention, the surgical robots can be equipped with various surgical instruments such as endoscopes, trocars, and cutting, gripping, or suturing instruments. The instruments are introduced by one or several robots into the patient's body via a port and the surgical intervention is then performed. During this process the robot system is controlled by a surgeon or possibly also by a surgical team via an input device.

The use of a trocar to make an artificial opening for a minimally invasive intervention is known to the prior art. In this case the trocar together with the trocar sleeve is pushed, for example, through the abdominal wall of a patient in order to establish an artificial access to the body cavity. The trocar is then withdrawn from the trocar sleeve, which remains inserted in the abdominal wall and keeps the access to the interior of the body open. The necessary surgical instruments (e.g., a scalpel, Potts scissors, an endoscope, etc.) as well as other surgical materials (e.g., needle, thread, etc.) can then be introduced into and/or taken out of the interior of the body through this access.

A standard trocar and trocar sleeve are described in U.S. 2009 03 06 697 A1. How a trocar is introduced into the interior of a body is illustrated in U.S. 2009 01 92 444 A1. In the cited publications it can be seen that the trocar sleeves are only loosely inserted in the abdominal wall. In robot-supported surgical interventions in particular, this has the disadvantage that the trocar sleeve may be moved in an uncontrolled manner in respect of its position or even slide out of the abdominal wall during a robot-supported surgical intervention.

Rather than with a trocar sleeve, an artificial access to the interior of a patient's body can also be established by means of so-called ports, as disclosed in U.S. 2010 249 694 or in WO 2011/163520. The function of a port is comparable to that of a trocar sleeve; however, a substantial difference from standard trocar sleeves lies in that, as a rule several surgical instruments can be introduced into a patient's body via a port. Here as well there is the danger of a port slipping or detaching from a patient's body if the port is used in conjunction with a surgical robot system for minimally invasive surgery.

In addition, U.S. Pat. No. 7,955,322 B2 discloses a robot arm 100 with a holding device 101 for a surgical instrument 103, on which device a trocar sleeve 102 is also fastened (see FIG. 1). The surgical instrument 103 fastened onto the holding device 101 is adjustable in its axial direction (arrow 105) by means of a carriage. The instrument 103 can thus be adjusted in the axial direction independently of the robot arm. During a movement of the robot arm 100, however, both the surgical instrument 103 and the trocar sleeve 102 are always moved simultaneously. With such an arrangement, however, it is not possible to effect an automatic instrument change. Hence changing the surgical instrument 103 always requires a manual intervention in order to exchange the instrument 103 and/or re-introduce it into the trocar sleeve 102.

DE 10 201 0 029 275 A1 discloses another robot system suited for surgical operations. In this robot system it is possible to effect an automatic instrument change by routing the surgical instrument by means of a robot into a trocar sleeve "loosely" inserted in the patient. In order to be able to actuate the robot in a precise manner so that the surgical instrument is inserted precisely into the trocar sleeve, the trocar sleeve is provided with a marker that is detected by a camera. The precise position data of the trocar sleeve are calculated from the image data by means of image processing software. Although an automatic instrument change is possible in principle, the procedure is relatively difficult and complicated. Furthermore, there is the danger of the trocar sleeve loosely inserted in the patient's body becoming detached as the instrument is being withdrawn from the patient.

DE 60 2004 004 995 T2 discloses a method for controlling a robot system for minimally invasive surgery in which several robot arms can be controlled by a pair of control arms. For example, a laparoscope, a camera, a pair of forceps, a scalpel, etc. can be mounted on one of the robot arms. However, it is also possible for a trocar to be moved by a robot arm.

Figure 2:
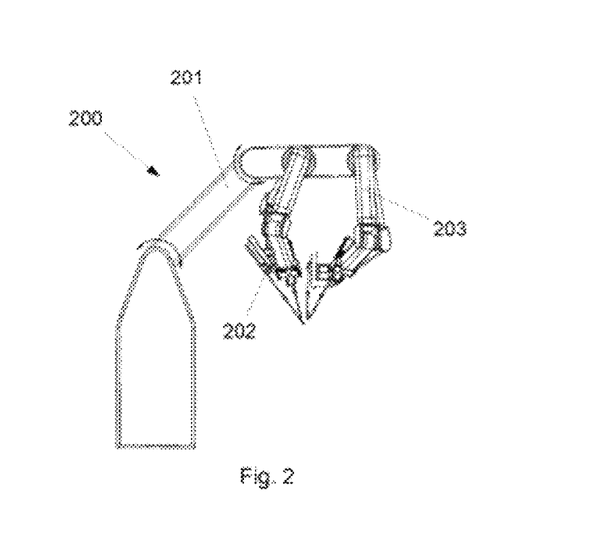
FIG. 2 a robot system known to the prior art with two robots that are each equipped with a surgical instrument.

Lastly, still another robot system for surgical interventions is known from WO 2011/149187 A2, which is constructed in the form of a multi-arm robot 200 (see FIG. 2). This robot comprises a main arm 201 to which two secondary arms 202 and 203 are attached. Each secondary arm 202, 203 can be equipped with a surgical instrument.

The object of the present invention is to be able to move or operate a port associated with a surgical robot system separately from the other surgical instruments associated with the robot system. In particular the aim is to create a robot system and a method for controlling a robot system by means of which an automatic instrument change can be effected without running the risk of a port inserted in a patient's body being moved in an uncontrolled manner or being pulled out during the procedure.

This object is achieved according to the invention by the features listed in the independent claims. Other embodiments of the invention emerge from the sub-claims.

According to the invention, a method for controlling a robot system for minimally invasive surgery is proposed, which comprises at least two robots, wherein a port that serves to keep an artificial access into the body of a patient open is operated by means of a first robot and a surgical instrument that is introduced through the port is operated by means of a second robot. The port and the surgical instrument are thus operated by different robots and can thus be moved independently of one another. Hence with such a robot system it is possible to introduce a surgical instrument automatically into the port or to execute an automatic instrument change. If the port is held securely by the associated robot during such a procedure, then there is no longer any danger of the port slipping or being pulled out of the patient's body during the instrument change.

In the context of this document, "port" means in particular any mechanism designed to provide access into a patient's body for one or more surgical instruments. According to the invention, ports can therefore be, for example, trocar sleeves or any other sleeve-like elements.

In the context of this document, "robot" means in particular a device with one or more articulated arms that can be moved by means of one or more actuators such as electric motors, for example.

The degree of freedom of the robot is thus determined by the number of its joints. The first robot, which holds the port, preferably has a number of degrees of freedom equal to the number of ways in which the port can be moved freely in space, i.e., a linear movement in all three spatial axes and pivot movements about all three spatial axes of a Cartesian coordinate system can be performed.

The separate controlling of the surgical instrument and of the port by means of different robots in principle offers the possibility of automatically moving the port synchronously during a movement (e.g., a pivot movement) of the surgical instrument, wherein the port will not exert a force on the surgical instrument or else exert a constant force, the possibility of damping a movement (e.g., a pivot movement) of the surgical instrument by means of the port, wherein the port restricts the movement of the instrument, or the possibility of blocking a movement of the instrument, wherein the port is fixed. The robot system of the invention is preferably designed such that the first robot that holds the port can be selectively operated in at least one of the following operating modes: a synchronous mode in which the port is moved automatically and essentially synchronously to a movement of the surgical instrument, a damping mode in which the port exerts a force that damps the movement of the surgical instrument, or a fixation mode in which the port is fixed in at least one of its degrees of freedom and can thus limit the movement of the surgical instrument in at least one, preferably in all, directions other than the axial direction.

The instrument can preferably be moved to a limited degree (e.g., tilted slightly) in the port if the instrument is accommodated in the port with clearance. The freedom of movement of the instrument is determined essentially by the shape of the port opening and the diameter of the shaft of the instrument or rather the clearance between the shaft and the port.

In a first embodiment of the invention, the respective operating mode can be selected by the user. For this purpose, provision can be made of a software input mask, an input panel, or any other input mechanism known to the prior art. The user can thus select one of the operating modes and switch between the individual operating modes as desired.

According to a preferred embodiment of the invention, the individual operating modes automatically set themselves in accordance with one or more parameters. Examples of parameters can include: the type of the surgical instrument attached to the second robot, the current procedure to be carried out, the nature of the movement (e.g., linear movement, pivot movement, or movement direction) of the surgical instrument, the speed of the movement, the control specification input by the user and/or the position of the surgical instrument.

For example, the type of the surgical instrument currently being used can be input manually into the robot system. However, preference is given to automatic recognition of the surgical instrument. In this case provision would be made of suitable means for automatic instrument recognition; the surgical instrument could be equipped with an RFID chip, for example. As an alternative, use can be made of any other prior art technology such as optical recognition by means of barcodes or image processing software capable of identifying the respective instrument.

The dependence of the operating mode of the first robot on the surgical procedure to be performed will be explained in more detail in the following, using an example: At the beginning of an operation, the abdominal wall of a patient is punctured using a trocar. An opening is pierced in the abdominal wall with the aid of the trocar, which is inserted in a trocar sleeve. During or after the puncture the trocar sleeve is introduced into the puncture site in such a way that it seats itself in the puncture site and provides access into the patient's body. The trocar is then removed from the trocar sleeve. During the puncture, the trocar must be moved in a specified axial direction and in particular may not slip or tilt while doing so. According to the invention, the trocar sleeve is therefore fixed in its position by the first robot, at least during the puncture. As the trocar is being withdrawn from the trocar sleeve, the latter should also be fixed in order to prevent it from being pulled out of the puncture site along with the trocar.

After a tool change, the operating mode of the first robot is then automatically switched from the fixation mode to another operating mode, e.g., the damping mode. In this case the changing of the operating mode can be triggered by the trocar being replaced with another instrument, which is detected by an implemented instrument recognition means, or for example by actuating a third robot equipped with another instrument in order to route the surgical instrument into the trocar sleeve.

For determining one or more of the other mentioned parameters such as the nature or speed of the instrument movement, the robot system preferably comprises a suitable sensor system with, e.g., a motion, speed, position, angle, and/or acceleration sensor.

In the synchronous mode, in principle the port can be actuated actively by the first robot, or the port can be carried along passively by the surgical instrument during a pivot movement thereof.

In the case of active actuation, the robot system is preferably designed such that a control specification performed by the operator of the robot system, in particular by a single movement of one hand, is converted into a first control command for controlling the first robot as well as into a second control command for controlling the second robot. Both robots are therefore actuated on the basis of the same control demand or rather movement. According to a special embodiment of the invention, the control command of one of the robots can be made available or rather transmitted to the control of the other robot. Optionally, two control commands for both robots could also be simultaneously generated from the operator's control specification.

In another embodiment of active actuation, the movement of the surgical instrument can be detected by sensors, for example by optical sensors such as a camera. In this case the sensor system records the instrument movement and generates corresponding movement data, which can be factored in by the control of the first robot in order to actuate the first robot and move the port in a corresponding manner.

The sensor system for detecting the movement of the surgical instrument can also have force or pressure sensors, which are mounted on the port or on the instrument and can detect forces acting between the surgical instrument and the port. If the surgical instrument presses against the port during a pivot movement, for example, the resulting force and if applicable also the position of the force effect can be analyzed in order to steer the first robot accordingly such that the port follows the pivot movement of the surgical instrument. As an alternative, the currents flowing in the electric motors of the first robot could also be analyzed to measure the forces or torques acting on the port. The embodiments described above can be designated as "active"

control because in each case control signals are generated for the first robot, with which the robot is then actuated.

As an alternative, provision could also be made of a purely passive operating mode, in which the port follows a pivot movement of the surgical instrument in a purely passive manner. In this case the first robot could be operated in such a way that, for example, it automatically yields to a sufficiently strong force exerted against the port by the surgical instrument so that the port is carried along in a purely passive manner by the movement of the surgical instrument.

As mentioned earlier, the first robot can be operated in such a way that the port synchronously follows a pivot movement of the surgical instrument, damps or in an extreme case blocks the movement of the surgical instrument. Preference is given to the intensity of the damping being adjustable by the user, for example via input into application software or by operating a hardware sensor (e.g., a slide or rotary adjuster).

According to a preferred embodiment of the invention, however, the damping automatically adjusts itself in response to one or more parameters. Examples of such parameters can include: the type of the surgical instrument attached to the second robot, the current surgical procedure to be performed, the nature of the movement (e.g., linear movement, pivot movement, or movement direction) of the surgical instrument, the speed of the movement, the control specification input by the user, the position of the surgical instrument and/or a personal ability of the user such as the surgeon's experience, for example. The intensity of the damping can preferably be varied.

With regard to the type of the surgical instrument, the damping during, for example, the use of a first instrument such as a trocar, can be considerably more intense than during the use of a second instrument such as a scalpel.

Furthermore, provision can be made such that the movement of the surgical instrument is more intensely damped at certain positions, for instance at the boundaries of a permissible work zone, than in the center of the work zone, where the consequences of possible errors in using the surgical instrument are less severe than at the work zone boundaries. The size of the permissible work zone can be defined by the user via an input mechanism such as a touchscreen, or it can be specified automatically by the system.

With regard to the nature of the movement of the surgical instrument, the robot system can be designed such that the port is more intensely or less intensely damped during movements of the surgical instrument in a certain direction or during pivot movements about a certain pivot axis than during movements in another direction and/or pivot movements about another pivot axis.

In principle there are several possibilities for fixing the port by means of the first robot. According to a first option, for example, provision can be made of a brake that locks the first robot when suitably actuated. According to another option, the first robot can also be controlled in such a way that it exerts a force that is directed against and is approximately equal to the force of the second robot such that said force exerted by said second robot is compensated.

According to a preferred embodiment of the invention, the port and the surgical instrument inserted in the port are adapted to one another in respect of their cross-section such that the surgical instrument is guided in the port with a certain clearance. Preference is given to this clearance being dimensioned such that the surgical instrument can be tilted at a specific angle relative to the axial direction of the port, which angle can be, e.g., between 5° and 60°, preferably between ca. 10° and 40°. This makes it possible to guide the surgical instrument freely within a geometrically specified work zone without having to move the port.

If a surgical instrument is to be routed into the port, preference is given to detecting the position and location of the port by sensors. Preference is given to a control of the second robot processing the relevant data such that the surgical instrument guided by the second robot can be routed precisely into the port. In order to facilitate the routing of the surgical instrument, the first robot can be actuated in such a way that the port vibrates slightly.

According to a special embodiment of the robot system, it is possible to define a work zone in which the surgical instrument may work. The work zone can be specified manually by the surgeon, e.g., via appropriate input on a touchscreen or by means of another input device. Optionally, a specific permissible work zone determined automatically on the basis of, say, the puncture site in the body of the patient, could also be allocated to each specific surgical instrument.

According to an embodiment of the invention, provision is made such that the first robot is controlled such that the port follows a movement of the surgical instrument (synchronously or with damping) as long as the surgical instrument is in the center of the permissible work zone, and such that the port will be automatically fixed if the surgical instrument moves into the boundary zone of the permissible work zone so that the boundary of the work zone is not crossed.

The invention also relates to a control device for controlling robots of a robot system for minimally invasive surgery, which has a first control unit for controlling a first robot, which operates a port that serves to provide access into the body of a patient, and a second control unit for controlling a second robot, which holds a surgical instrument, wherein the first control unit can run the robot in different operating modes. In particular, the control unit can be operated in a first operating mode in which the port is fixed, or in another operating mode in which the port follows a pivot and/or a positioning movement of the surgical instrument, wherein the guiding of the port can be synchronous to the instrument or damped.

The first control unit preferably comprises means, e.g., an algorithm, for controlling the robot in at least one of the following operating modes: a synchronous mode, a damping mode, or a fixation mode.

Lastly, the invention also relates to a robot system that has such a control device.

BRIEF DESCRIPTION OF THE DRAWINGS

The invention will be explained in more detail in the following by means of examples and with reference to the appended drawings. Shown are.

EMBODIMENTS OF THE INVENTION

Figure 1:
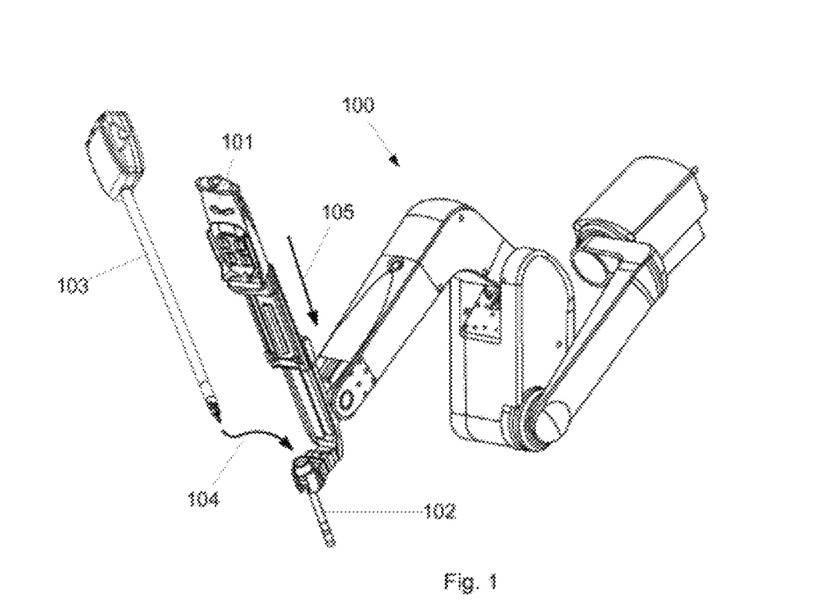
FIG. 1 a robot known to the prior art with a carriage for positioning a surgical instrument and a holder for a trocar sleeve.

See the introductory part of the description for the explanation of FIGS. 1 and 2.

Figure 3:
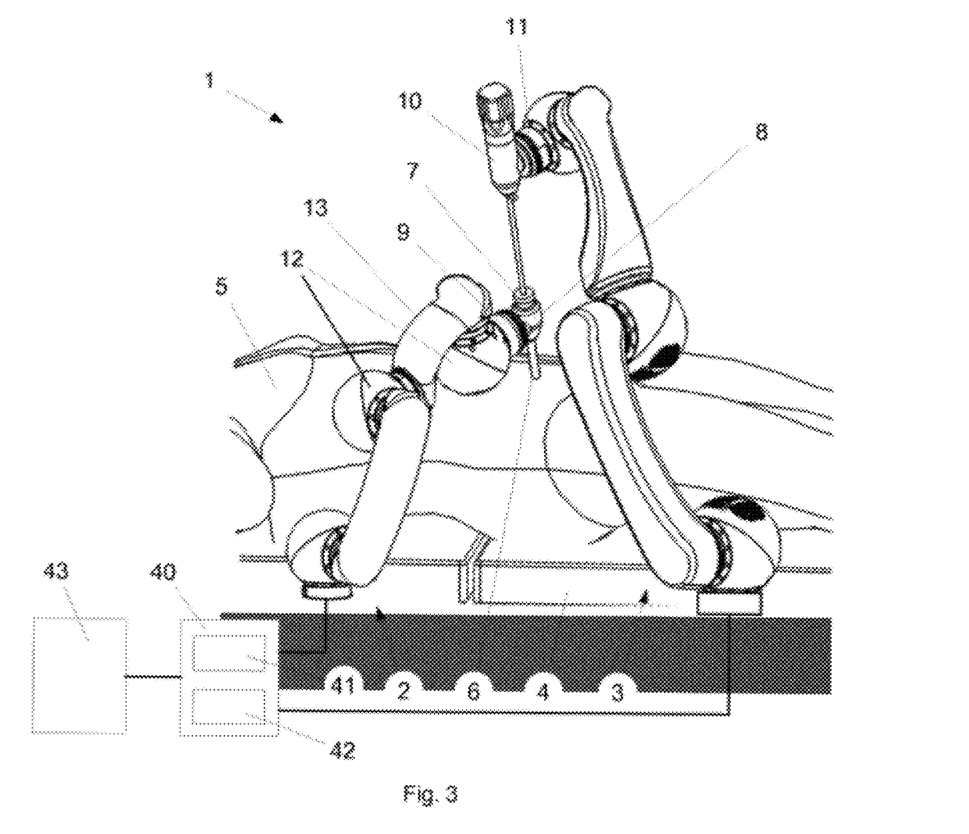
FIG. 3 a robot system according to the invention with two robots, one of which is equipped with a surgical instrument and the other of which is equipped with a port.

FIG. 3 shows an exemplary embodiment of a robot system with two robots 2, 3, wherein the first robot 2 is equipped with a port 7 and the second robot 3 is equipped with a surgical instrument 10. Each robot comprises two robot arms 13 that can be rotated and pivoted via joints 12. In the exemplary embodiment illustrated, each robot 2, 3 has in total six degrees of freedom so that each element 7, 10 held by each robot 2, 3 is freely movable in space. Both robots 2, 3 are fastened to an operating table 4 on which the patient 5 undergoing treatment is lying.

The first robot 2 has on its free head end a holder 8, which can be detachably fastened in a receptacle 9. The holder 8 is designed such that a port 7 can be received without clearance, i.e., there is a fixed connection between the port 7 and the first robot 2. The second robot 3 likewise comprises a receptacle 11 to which a surgical instrument 10 can be attached. The surgical instrument 10 can be a gripping, holding, cutting, sawing, grinding, connecting, joining, or other tool such as a scalpel, Potts scissors, forceps, a trocar, etc.

In the example illustrated, the port 7 is inserted in a puncture site 6 in the abdominal wall of the patient 5 and provides access into the interior of the body for the surgical instrument 10.

The two robots 2, 3 can be controlled by a surgeon or user by means of an input device 43. Said input device 43 can be, for example, a joystick, an imaging system, a mouse, a touchpad, or any other standard input device.

The control demands performed by the user are converted by a control device 40 into corresponding control commands for the individual actuators of the robots 2, 3. In the exemplary embodiment illustrated, a first control unit 41 for the first robot 2 and a second control unit 42 for the second robot 3 are integrated in the control device 40 in the form of control software. However, the control units 41, 42 can also be arranged elsewhere, where appropriate also distributed over several control devices.

By operating the port 7 and the surgical instrument 10 separately by means of a first and a second robot 2 and 3, respectively, it is possible to move the port 7 independently of the surgical instrument 10 or when necessary also to fix it. It is furthermore possible to damp or completely block a movement of the surgical instrument 10 by means of the port 7. However, the port 7 can also be moved by means of the first robot 2 in such a way that it synchronously follows a movement of the surgical instrument 10.

Figure 4:
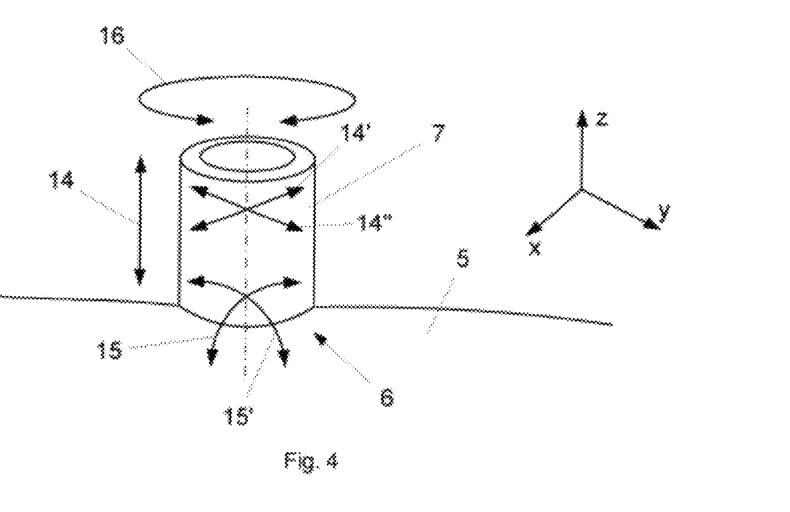
FIG. 4 a magnified view of the port of FIG. 3 and the possible degrees of freedom of movement of the port.

FIG. 4 is a magnified view of the port of FIG. 3 and the various movement and/or pivot directions within a Cartesian coordinate system with the axes x, y, z; in the directions and/or about the axes of which the port 7 can in principle be moved. In the present case the port 7 is freely movable in space. A movement in the direction of the orthogonal axes x, y, z is represented by the arrows 14, 14', and 14". The pivot movements about the coordinate axes are represented by the arrows 15, 15', and 16. For carrying out the minimally invasive operation, the port 7 is inserted in the puncture point 6 of the patient 5 (also called the trocar point). So as not to exert excessive stress on the puncture point 6, in an advantageous manner all other movements along with the pivot movements about the x and y axes can be limited to a necessary minimum. Owing to the separate drive of the port 7 and of the surgical instrument 10, the port 7 can be moved independently of the surgical instrument 10 and the surgical instrument 10 can likewise be moved independently of the port 7. For example, the instrument 10 can be rotated about its longitudinal axis by the robot 3 without the port 7 being turned as well. Hence the end effector 19 or rather the surgical instrument 10 can not only be rotated about the axis 21 by a rotary movement of the instrument shaft (see FIG. 6), but also by a pivot movement of the robot 3, which pivots the entire instrument 10 including the holder 11. A separate instrument drive that rotates the end effector 19 about the longitudinal axis 21 of the instrument 10 can be dispensed with in this case.

Figure 5:
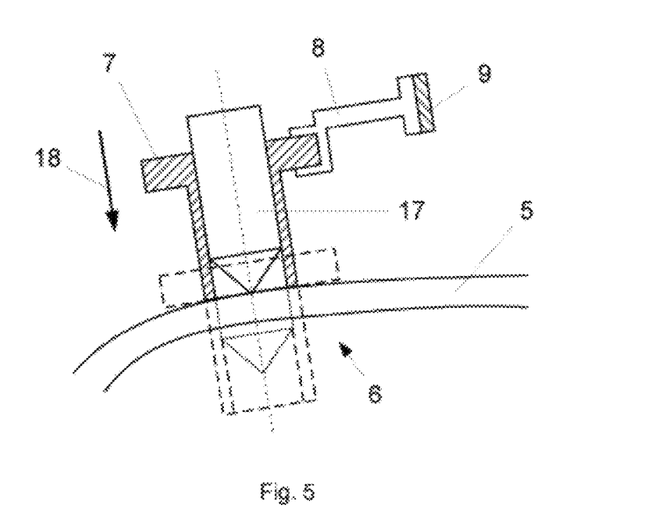
FIG. 5 different positions of the port during the puncturing of the abdominal wall of a patient.

FIG. 5 shows different states during the puncturing of the abdominal wall of a patient 5 by means of a trocar 17. First the port 7 is positioned at the desired puncture site 6 and then fixed in this position with the aid of the first robot 2. Afterwards the trocar 17 is introduced into the port 7 and the abdominal wall is penetrated by pushing the trocar 17 forwards. During or after the penetration of the abdominal wall, the port 7 is guided into the resulting opening by the robot 2 so that it seats firmly in the puncture site 6 and keeps the opening open. The final position of the port 7 is schematically illustrated by a dashed line. The port 7 is then fixed in this position by means of the first robot 2. Afterwards the trocar 17 is withdrawn from the port 7. In other words, while the instrument or rather the trocar 17 was being moved to penetrate the abdominal wall, the port 7 was first fixed, then moved, and then fixed again. The movement of the port 7 thus took place independently of the movement of the trocar 17.

In principle there are several options for fixing the port 7. According to a first option, the robot 2 comprises a brake with which the robot 2 can be locked. Suitable braking mechanisms are sufficiently known to the prior art.

According to a second option, the first robot 2 can also be run in such a way that it generates a counter force or counter torque that is directed against and is approximately equal to the force or torque exerted by the second robot 3 such that the forces or torques cancel each other out.

According to a preferred embodiment, the control 41 of the robot 2 automatically sets the fixation of the port 7 for every possible degree of freedom (see FIG. 4), wherein the respective fixation can be dependent upon various parameters such as the type of the surgical instrument 10, the nature of the procedure to be performed, the nature of the movement (linear movement, pivot movement, movement in a specific direction, etc.) of the surgical instrument, the speed of the surgical instrument 10, the position of the surgical instrument 10 and/or the experience of the surgeon.

Figure 6:
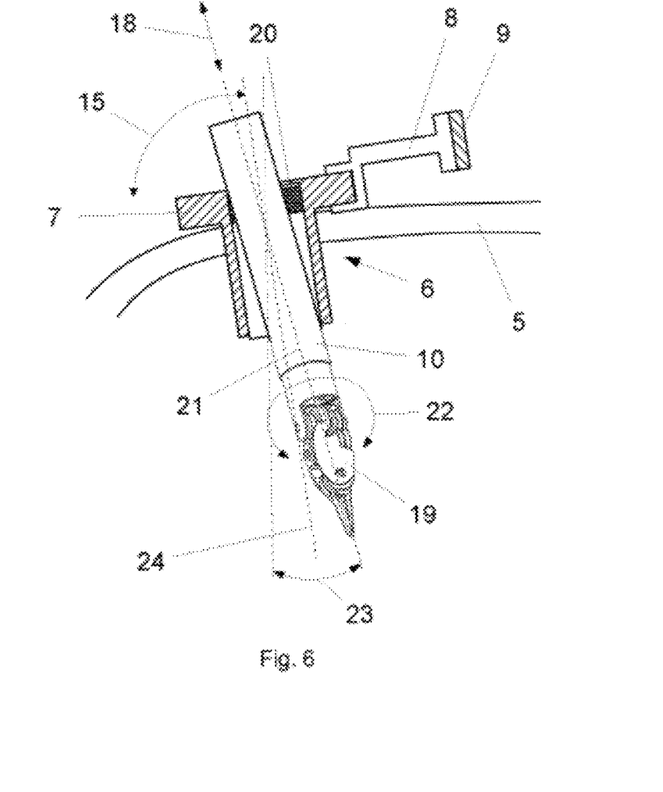
FIG. 6 the work zone of a surgical instrument that is introduced into the abdominal cavity of a patient, in an operating mode in which the port is fixed.

FIG. 6 shows a state during an operation in which a pair of Potts scissors is being introduced via a seal 20 present in the port 7 and through the port 7 into the abdominal cavity of a patient 5. The longitudinal axis of the instrument 10 and the longitudinal axis of the port 7 are designated with the reference signs 21 and 24, respectively.

As can be discerned, the shaft of the surgical instrument 10 has a clearly smaller diameter than the through-opening of the port 7 so that the instrument 10 is received in the port 7 with clearance. Owing to the clearance, it is possible to tilt the surgical instrument 10 slightly within a limited work zone 23. The size of the work zone 23 is specified in particular by the clearance between the instrument 10 and the port 7 as well as by the length of the port 7. The surgical instrument 10 can typically be pivoted about an angle ranging from, say, 5° to 60° and in particular from 10° to 40°. Furthermore, the surgical instrument 10 can also be rotated about its longitudinal axis 21 in the direction of the arrow 22 and/or moved up and down along the longitudinal axis 21 in the direction of the arrow 18.

Figure 7:
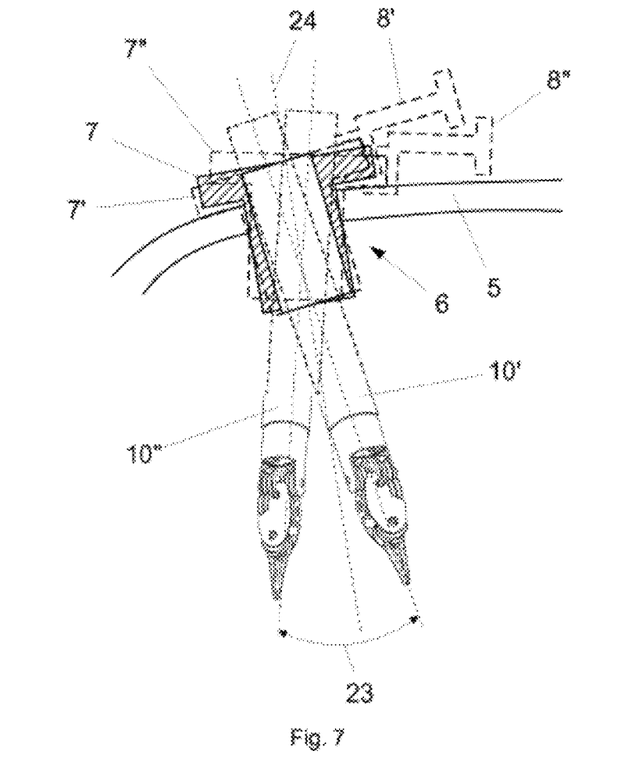
FIG. 7 the work zone of a surgical instrument that is introduced into the abdominal cavity of a patient, in an operating mode in which the port follows a pivot movement of the surgical instrument.

If on the other hand the port 7 is not fixed in a stationary position by the robot 2, the work zone 23 can be widened considerably, as illustrated in FIG. 7. For this purpose, the port 7 is tilted or rather a passive tilting is permitted by the robot 2, as illustrated by means of dashed lines 7', 7", and 8' or 8". The surgical instrument 10 can thus be pivoted to and from positions 10' and 10".

The tilt angle is advantageously limited in order to minimize the risk of injury to the patient. For instance, specific limit values can be programmed into the control 40. If a specific limit value in a specific tilting or pivoting direction is reached by the port 7, the robot 2 can promptly fix the port 7 in this direction.

In principle it is possible to operate the port 7 by the robot 2 such that it is moved synchronously with the instrument 10, at least within a certain path and/or in at least one movement direction shown in FIG. 4. In other words, the port 7 is moved or guided in a corresponding manner during a tilting and/or pivoting of the instrument 10. For example, the clearance between the instrument 10 and the port 7 could consequently be maintained by the robot 2 during movements of the instrument. As a result no force is exerted on the surgical instrument 10 by the port 7 (and vice versa).

The assignment of the movements of the tool 10 during which the port 7 is either blocked or synchronously moved thereto is freely programmable and can be filed in the robot system. For example, the port 7 should not be displaceable along the axis of the tool 10 during axial movements 14 thereof (see FIG. 4), but should be moved with the tool 10 if pivot movements 15, 15' are executed with said tool 10.

To this end, the robot system can be actively actuated. It is preferably designed in such a way that a control specification input by the operator of the robot system will be converted into a first control command for controlling the first robot 2 as well as into a second control command for controlling the second robot 3. Both robots 2 and 3 can thus be actuated on the basis of the same control specification.

However, the port 7 can also be operated in such a way that it damps a movement of the surgical instrument 10. In principle the intensity of the damping can be freely specified. For example, a specific damping can be set as a default in the control of the first robot 2. Optionally the damping can also be varied by the user, for example by a corresponding input at a terminal. In principle the damping can be increased sufficiently high for each degree of freedom of the port 7 such that the port 7 is completely blocked in every movement direction, or reduced sufficiently low for each degree of freedom of the port 7 such that the port 7 synchronously follows the instrument 10 freely in every movement direction.

According to a preferred embodiment, the damping sets itself automatically for each possible degree of freedom of the port 7 (see FIG. 4), wherein the intensity of the damping can be dependent upon various parameters such, e.g., the type of the surgical instrument 10, the nature of the movement of the surgical instrument (linear movement, pivot movement, movement in a specific direction, etc.), the speed of the surgical instrument 10, the position of the surgical instrument 10 and/or the experience of the surgeon.

For instance, provision can be made such that the damping during the use of a first surgical instrument 10 is more intense or less intense than during the use of a second surgical instrument. Provision can be made of a sensor system (e.g., a RFID sensor) for recognizing the respective instrument 10.

Additional provision could be made of variable damping for certain surgical interventions, e.g., for a puncture or for making an incision. The intensity of the damping can also depend upon the position of the surgical instrument, wherein in principle a more intense damping should be selected in the boundary zone of the work zone 23 than in the center of the permissible work zone 23 in order to prevent possible injury to surrounding organs. Lastly, provision can also be made of a sensor system for person identification, which recognizes the user automatically or after a suitable login by the latter and selects a person-dependent level of damping.

Hence the port 7 can be moved synchronously to the movement of the surgical instrument 10, damp a movement of the surgical instrument 10, or block the movement of the surgical instrument 10 as a function of one or more of the aforementioned known parameters.

Figure 8:
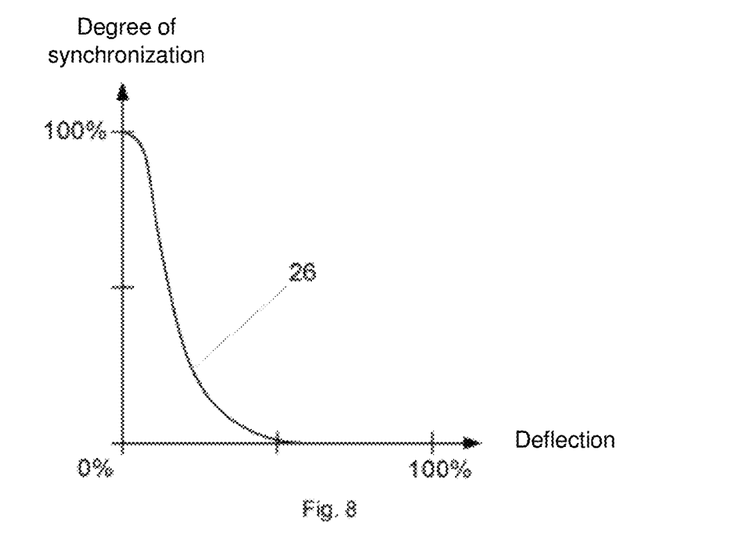
FIG. 8 an example showing how the degree of synchronization of the port changes as a function of the deflection of the surgical instrument.

FIG. 8 shows an example of how the degree of synchronization between the port 7 and the surgical instrument 10 changes as a function of the location of the end effector 19. In the example illustrated, the surgical instrument 10 is deflected, by being tilted, swiveled or pivoted, to an increasingly greater degree from a position in which the longitudinal axis 18 of the surgical instrument 10 aligns with that of the port 7. With a slight deflection (e.g., less than 10°), the first robot 2 is controlled in such a way that the port 7 essentially follows the pivot movement of the surgical instrument 10 synchronously. With increasing deflection of the surgical instrument 10, the degree of synchronization decreases linearly, or rather the damping increases in a corresponding manner. The port 7 is then fixed starting at ca. 50% of the permissible deflection of the surgical instrument 10. In this state the port 7 functions as a (mechanical) stop for the instrument 10. A sudden braking or blocking of the instrument 10, which could damage it, is avoided by the continuous damping.

If the deflection of the instrument 10 is reversed, the degree of synchronization of the corresponding degree of freedom will increase such that the port 7 regains its mobility until the port 7 follows the instrument 10 in an unrestricted (non-damped) manner. The instrument 10 is then freely movable once again.

In principle a characteristic curve such as the one shown in FIG. 8 can be freely specified. The characteristic curve can change as a function of one or more of the aforementioned parameters. Hence the characteristic curve can be defined in a person-dependent manner, in order to define a narrower work zone 23 for less-experienced surgeons than for experienced surgeons, for example. The damping function can advantageously be applied separately for each degree of freedom of the robot 2.

Figure 9:
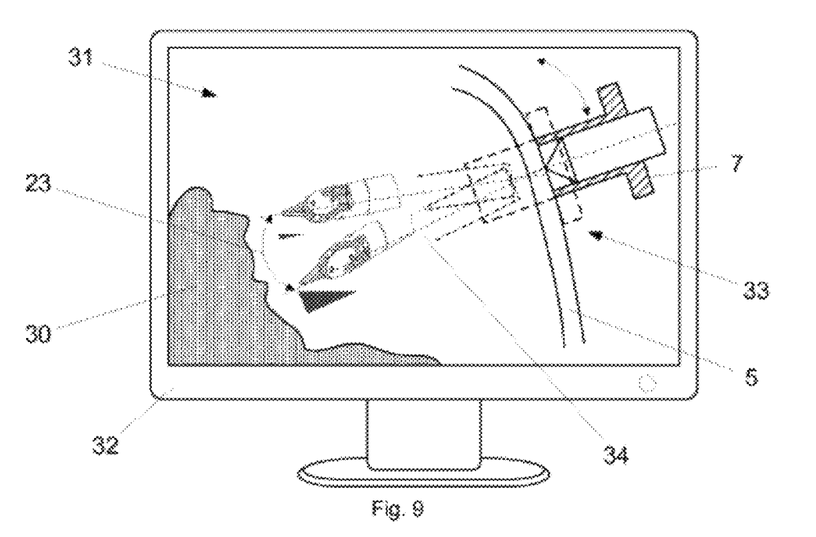
FIG. 9 an illustration of a surgical intervention on a monitor.

FIG. 9 shows a monitor 32 on which the position of a port 7 inserted in the abdominal wall of a patient 5, a trocar, and a virtual surgical instrument 34 are displayed. Because the robot controls 41 and 42 of the two robots 2 and 3 can communicate with one another, the geometric data of the trocar 17 and/or of the port 7 are known to the robot system so that a potential insertion position 33 can be calculated therefrom. Furthermore, the work zone 23 of a virtual surgical instrument 34 can be calculated with this insertion position factored in. For example, on the basis of the potential insertion position 33 of the port 7 it is possible to ascertain whether the tissue 30 to be operated on lies within the work zone 25 of the selected instrument before actually forming the opening 6 in the patient 5 (i.e., before the puncture of the trocar 17). In doing so the maximum permissible pivot angles of the port 7 can also be factored in. In addition the surgical instrument 34 and the work zone 25 can be displayed in a virtual environment 31 on the monitor 32.

If the work zone 23 is not suitable for the surgical intervention to be performed, the surgeon can adjust the insertion position 33 by moving the port 7 to another place. Preference is given to the surgical instrument and the virtual work zone 23 likewise being displayed at the new position. If the current insertion position 33 corresponds to the insertion position desired by the surgeon, the surgeon can switch the port 7 to the fixation mode and pierce the abdominal wall of the patient 5 with the trocar 17. With the virtual representation of the surgical instrument and/or of the work zone 25, it is possible to ensure that the body of the patient 5 is punctured at the right place, i.e., the one from which the tissue 30 to be operated on can be treated.

Figure 10:
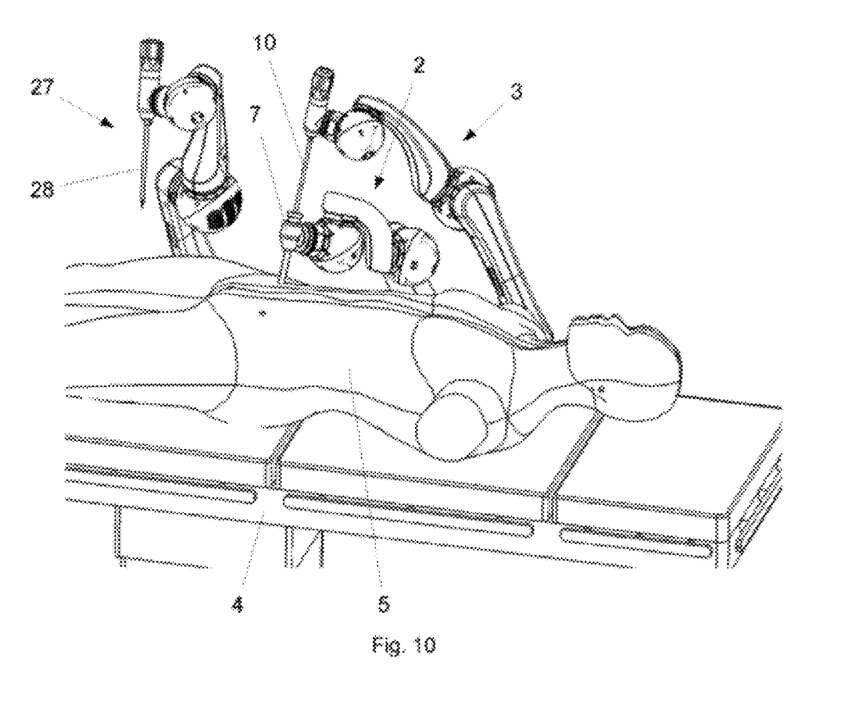
FIG. 10 a robot system of the invention with a total of three robots.

FIG. 10 shows a robot system with three robots 2, 3, 27, of which the first robot 2 likewise guides a port 7, and the second robot 3 holds a surgical instrument 10, and the third robot 27 holds another surgical instrument 28. In the situation illustrated, the surgical instrument 10 held by the second robot 3 is introduced through the port 7 into the body of the patient 5. In order to effect an automatic instrument change, the first robot 2 is operated in the fixation mode so that the port 7 will not slip or be pulled from the body of the patient 5 as the instrument 10 is being withdrawn. To this end, the robot 3 guides the instrument 10 out of the port 7 and brings it into a resting position such as the one shown in FIG. 11. If necessary, the robot 2 can now correct or alter the position of the port 7 for introducing the instrument 28. After adjusting the position of the port 7, the first robot 2 is switched back into the fixation mode so that the port 7 does not shift its position during the routing of the instrument 28. The port 7 can vibrate slightly in order to facilitate the routing of the instrument 28.

The robot 27 then activates and routes the instrument 28 into the port 7. For doing so the robot 27 can use the position and/or location information of the port 7, which are known from the control software of the first robot 2. For example, all movements of the robot system can be logged. The robot 27 can thus introduce the instrument 28 precisely into the port 7. The first robot 2 can let the port 7 vibrate slightly in order to facilitate the routing.

After the introduction of the instrument 28 into the port 7, the first robot 2 can be switched to the synchronous or damping mode. The specifications governing the mode in which the port 7 is operated can depend upon various parameters, as described above.

If the port 7 is switched into the synchronous mode or damping mode for at least one degree of freedom, the robot system then ensures that the robot 2 only lets the port 7 automatically follow the movements of the respective instrument 10, 28 with which the port is associated. On the basis of the position of the port 7 and of the instruments 10, 28, the robot system automatically knows which instrument is associated with the port 7 and which instrument 10, 28 should follow the port 7 accordingly. According to a preferred embodiment of the invention, the drive commands of all other robots 3, 27 are transferred to the robot control of the first robot 2 so that for synchronizing the port 7, the control of the first robot 2 can automatically use the drive commands of the respective robot 3, 27 whose instrument 10, 28 is inserted in the port 7. According to the invention it is thus possible to synchronize the port 7 or robot 2 with different robots 3, 27 or instruments 10, 28, respectively. According to the invention, after effecting a tool change it is also possible to switch the port 7 automatically to the various operating modes (fixation mode, synchronous mode, and damping mode).

Figure 11:
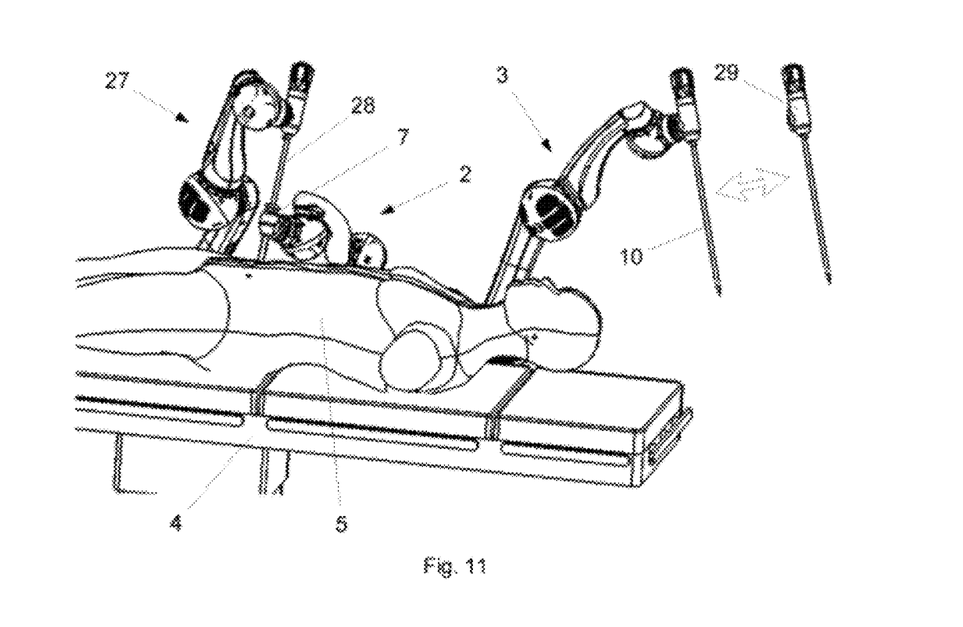
FIG. 11 a schematic illustration of a change of instruments on one of the robots.

Finally, FIG. 11 shows a state in which the surgical instrument 28 of the robot 27 is routed into the port 7. The second robot 3 is in a standby position, in which the tool 10 can be changed. In the present case, the surgical instrument 10 will be replaced with another instrument 29. So as to be able to work with the instrument 29 in the further course of the operation, another tool change will be effected in the manner described previously.

Figure 12:
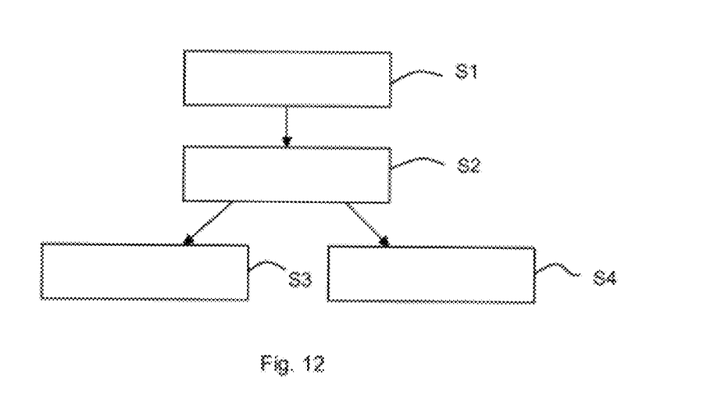
FIG. 12 various method steps of a method for automatically controlling a surgical instrument and a port with different robot arms.

Finally still, FIG. 12 shows different method steps of a method for automatically controlling a surgical instrument and a port with different robot arms. A control movement made by a user is detected in a first step S1. Depending upon the configuration of the robot system, for this purpose provision can be made of a joystick, an imaging system, a mouse, a touchpad, or other prior art input mechanism.

The operating mode (synchronous, damping, or blocking mode) is defined in step S2. For example, the operating mode can be specified by the user, or it results from different automatically identified state variables or parameters, as described previously.

Depending upon the nature and dynamics of the control demand and also depending upon the operating mode, corresponding control commands for the individual actuators of a first robot (e.g., robot 2) and for the individual actuators of a second robot (e.g., robot 3) are generated in steps S3 and S4, respectively. The two robot arms then move automatically in accordance with the control movement performed by the user and in dependence upon the specified operating mode.

The invention claimed is:

1. A method for controlling a robot system for minimally invasive surgery, which comprises at least two robots, the method comprising the following steps:
   operating a port, which serves to provide access into the body of a patient, by means of a first robot, which is configured to move the port freely in space; and
   operating a surgical instrument, which is designed to be introduced into the body of a patient through the port, by means of a second robot, which is configured to move the surgical instrument freely in space and independently of the first robot.

2. The method as in claim 1, wherein the first robot is operated during certain operating phases in a synchronous mode, in which the port automatically and more or less synchronously follows a pivot movement of the surgical instrument.

3. The method as in claim 1, wherein a control input performed by an operator of the robot system is converted to a first control command for controlling the first robot and also to a second control command for controlling the second robot.

4. The method as in claim 1, wherein the first robot is operated during certain operating phases in a damping mode, in which the port damps at least one degree of freedom of the surgical instrument guided through said port.

5. The method as in claim 4, wherein the intensity of the damping depends upon the nature of the surgical procedure to be performed, the nature of the movement of the surgical instrument, the speed of the surgical instrument, the position of the surgical instrument, and/or personal ability of the surgeon.

6. The method as in claim 4, wherein the intensity of the damping is adjustable.

7. The method as in claim 1, wherein the first robot is operated during certain operating phases in a fixation mode, in which at least one degree of freedom of the port is fixed.

8. The method as in claim 1, wherein the first robot is operated either in a synchronous mode or in a damping mode or in a fixation mode, depending upon the type of the surgical instrument, the nature of the current surgical procedure to be performed, the nature of the movement of the surgical instrument, and/or the position of the surgical instrument.

9. The method as in claim 7, wherein the port is fixed when a brake integrated in the first robot is actuated or when the first robot is operated in such a way that it exerts a force that is directed against and is approximately equal to the one of the second robot.

10. The method as in claim 7, wherein the operating mode of the robot system in which the port is fixed and/or an operating mode in which the port is movable can be set by the user.

11. The method as in claim 8, wherein the robot system automatically switches to and from the fixation mode, synchronous mode, and/or damping mode.

12. The method as in claim 1, wherein the position and/or the location of the port is/are detected by sensors and/or logged and the data relevant thereto are processed by a control of the second robot in order to route the surgical instrument guided by the second robot into the port.

13. The method as in claim 12, wherein the first robot is controlled in such a way that the port vibrates during the routing of a surgical instrument into the port.

14. The method as in claim 7, wherein a work zone is defined in which the surgical instrument may work, and that the first robot is operated in such a way that the port follows a movement of the surgical instrument as long as the surgical instrument is within the work zone, and the port is fixed if the surgical instrument moves into a boundary zone of the work zone so that the surgical instrument does not go beyond the boundary of the work zone.

15. The method as in claim 14, wherein at least one degree of freedom of the port is increasingly damped as the surgical instrument moves closer to the boundary zone of the work zone.

16. Control device for controlling robots of a robot system for minimally invasive surgery, comprising:
   a first control unit for controlling a first robot, which operates a port that serves to provide access into the body of a patient, wherein the first robot is configured to move the port freely in space; and
   a second control unit for controlling a second robot, which operates a surgical instrument that is designed to be introduced into the body of a patient through the port, wherein the second robot is configured to move the surgical instrument freely in space and independently of the first robot; and
   wherein the first control unit has means for driving the robot either in a first operating mode in which at least one degree of freedom of the port is fixed and/or in a second operating mode in which the port synchronously follows a movement of the surgical instrument, and/or in a third operating mode in which at least one degree of freedom of the port is damped.

17. A robot system with at least two individually controllable robots, comprising a control device as claimed in claim 16.

* * * * *